United States Patent [19]
Mendolia et al.

[11] Patent Number: 5,911,975
[45] Date of Patent: Jun. 15, 1999

[54] ANTIPERSPIRANT AND DEODORANT COMPOSITIONS CONTAINING POLY (ETHENYLFORMAMIDE) THICKENING AGENT

[75] Inventors: Michael S. Mendolia, Bridgewater; Paul J. Vincenti, Jefferson; Anthony Esposito, Roselle, all of N.J.; Joseph Edward Glass, Fargo, N. Dak.

[73] Assignee: Colgate-Palmolive Company, New York, N.Y.

[21] Appl. No.: 08/728,183

[22] Filed: Oct. 9, 1996

Related U.S. Application Data

[XX .
[60] Provisional application No. 60/004,441, Oct. 13, 1995.
[51] Int. Cl.⁶ .............................. A61K 7/32; A61K 7/00
[52] U.S. Cl. ................................ 424/65; 424/66; 424/67; 424/68; 424/400; 424/401; 424/DIG. 5
[58] Field of Search ................... 424/65, 66, 67, 424/68, 400, 401, DIG. 5

[56] References Cited

U.S. PATENT DOCUMENTS

| | | | |
|---|---|---|---|
| 2,210,014 | 8/1940 | Teller | 424/68 |
| 3,148,125 | 9/1964 | Strianse et al. | 424/64 |
| 3,255,082 | 6/1966 | Barton | 424/68 |
| 3,574,822 | 4/1971 | Shepherd et al. | 424/47 |
| 3,862,310 | 1/1975 | Quasius | 510/126 |
| 4,011,311 | 3/1977 | Noomen et al. | 424/65 |
| 4,116,913 | 9/1978 | Barabas | 524/96 |
| 4,331,609 | 5/1982 | Orr | 424/66 |
| 4,383,988 | 5/1983 | Teng et al. | 424/68 |
| 4,564,556 | 1/1986 | Lange | 501/33 |
| 4,673,570 | 6/1987 | Soldati | 424/66 |
| 4,801,447 | 1/1989 | Gum | 424/68 |
| 4,937,069 | 6/1990 | Shin | 424/66 |
| 4,948,578 | 8/1990 | Burger et al. | 424/68 |
| 5,069,897 | 12/1991 | Orr | 424/66 |
| 5,102,656 | 4/1992 | Kasat | 424/66 |
| 5,208,074 | 5/1993 | Kosal | 427/389 |
| 5,270,379 | 12/1993 | McAndrew et al. | 524/555 |
| 5,478,553 | 12/1995 | Chandran | 424/70.17 |
| 5,487,887 | 1/1996 | Benfatto | 424/66 |
| 5,500,209 | 3/1996 | Ross et al. | 424/66 |
| 5,512,645 | 4/1996 | Sawayama et al. | 526/264 |
| 5,575,990 | 11/1996 | Benfatto | 424/65 |
| 5,603,925 | 2/1997 | Ross et al. | 424/65 |
| 5,635,166 | 6/1997 | Galleguillos et al. | 424/66 |
| 5,643,559 | 7/1997 | Eigen et al. | 424/67 |

FOREIGN PATENT DOCUMENTS

| | | |
|---|---|---|
| 44 41 940 A1 | 6/1995 | Germany . |
| 54-140714 | 11/1979 | Japan . |
| WO92/05767 | 4/1992 | WIPO . |

*Primary Examiner*—Shelley A. Dodson
*Attorney, Agent, or Firm*—William I. Solomon; Richard J. Ancel; Rosemary M. Miano

[57] ABSTRACT

Disclosed is a cosmetic composition (solid or liquid, for example, including sticks and gels) containing an antiperspirant active aluminum-containing material, such as aluminum chlorohydrate, in a solvent therefor, and also containing poly(ethenylformamide) as a thickening agent of the composition. This composition can be an antiperspirant composition, where it contains an antiperspirant effective amount of the antiperspirant active aluminum-containing material, and can be applied to axillary regions of a human to reduce perspiration therefrom. Ammonium acetate can also be incorporated in the composition, to firm up the composition. The composition can be in the form of a gel, dispensed by extruding the gel through pores or slots in the top of a dispensing container. The composition can be clear and transparent, without the need of refractive index matching to achieve clarity.

40 Claims, No Drawings

5,911,975

ANTIPERSPIRANT AND DEODORANT COMPOSITIONS CONTAINING POLY (ETHENYLFORMAMIDE) THICKENING AGENT

This application claims priority under 35 USC 119(e)(1) of provisional application Ser. No. 60/004,441, filed Oct. 13, 1995.

BACKGROUND OF THE INVENTION

The present invention is directed to a cosmetic composition (for example, a solid or liquid deodorant and/or antiperspirant composition) containing an antiperspirant active aluminum-containing material, such as an antiperspirant active aluminum-containing salt. The composition of the present invention can be used to combat body malodor, e.g., in axillary regions of the human body, by applying the composition to the human body (for example, to the skin, in axillary regions of the body).

The present invention is particularly directed to a solid or liquid antiperspirant composition containing an antiperspirant active aluminum-containing salt (for example, conventional aluminum chlorohydrate or aluminum-zirconium salts), the antiperspirant active aluminum-containing salt being included in the composition in antiperspirant effective amounts. However, the present invention is not limited to solid or liquid antiperspirant compositions, including within its scope solid or liquid cosmetic compositions, including solid or liquid deodorant compositions, where, for example, the antiperspirant active aluminum-containing material is included in the composition in amounts insufficient to provide an antiperspirant effect, yet sufficient to provide a deodorant effect. The present invention is especially directed to a solid or liquid cosmetic (e.g., deodorant and/or antiperspirant) composition having the aluminum-containing active ingredient incorporated therein, which is stable even in the presence of acidic antiperspirant active aluminum-containing materials. The present composition, preferably, is translucent or clear, but need not be translucent or clear.

Antiperspirant products are well known in the art. Antiperspirant products have appeared in the marketplace in various dosage forms, such as sticks, gels, roll-ons, aerosols and creams. Generally, these dosage forms include a solution of the active ingredient in a suitable solvent, a suspension of the active ingredient in a non-solvent, or a multiphasic dispersion or emulsion in which a solution of the active ingredient is dispersed in some continuous phase or in which the solubilized active ingredient constitutes a continuous phase.

Of the above-referred-to dosage forms, the roll-on is an example of a liquid form composition, the stick form is an example of a solid form, and the gel form is a thickened form which may or may not be a solid (e.g., under some circumstances, gels can flow). The stick form can be distinguished from a gel in that, in a stick, the formulated product can maintain its shape for extended time periods outside the package, the product not losing its shape significantly (allowing for some shrinkage due to solvent evaporation). Adjustment of amounts of gelling or thickening agents such as bentones, fumed silica or polyethylene, or stearyl alcohol and castor wax, can be used in order to form a gel or stick.

Gels can be suitably packaged in containers which have the appearance of a stick, but which dispense through apertures (for example, slots or pores) on the top surface of the package. These gel products have also been called soft sticks or "smooth-ons", and hereinafter these are generically called "gels". Reference is made to U.S. Pat. No. 5,102,656 to Kasat, U.S. Pat. No. 5,069,897 to Orr, and U.S. Pat. No. 4,937,069 to Shin, each of which disclose such gels, including physical characteristics thereof such as viscosity and hardness. The contents of each of these three U.S. patents are incorporated herein by reference in their entirety.

Recently, there has been significant activity in developing clear and translucent antiperspirant sticks and gels. Clear or translucent antiperspirant sticks consisting essentially of a solution of the active antiperspirant material in a polyhydric alcohol vehicle, gelled by dibenzylidene monosorbitol acetal, have been disclosed. Since the gelling agent is inherently unstable in an acidic environment, and since conventional active antiperspirant materials are acidic, much work has been involved in discovering suitable stabilizing or buffering agents to prevent or slow down acid attack on the acetal gelling agent.

Such work has not been completely successful. Moreover, these clear or translucent antiperspirant sticks, containing the acetal gelling agent and including a solubilized active antiperspirant material, have the disadvantage of being inherently tacky. Thus, development work in connection with these clear or translucent antiperspirant sticks containing the acetal gelling agent has focused on discovering suitable anti-tack agents for this dosage form. However, since acid hydrolysis of the gelling agent occurs more rapidly in aqueous solutions, formulators have been forced to avoid using water in the formulations. This severely restricts the ability of the formulator to develop cosmetically elegant formulations which are simultaneously chemically stable, optically clear, low in tack, low in residue and which have acceptable application aesthetics.

Clear or translucent antiperspirant gels (which have been dispensed from containers having the appearance of a stick) have been marketed, consisting of viscous, high internal phase emulsions. These gels exhibit some advantages over the aforementioned acetal-based clear sticks, in that the selection of formulation ingredients is less restricted (for example, water can be used), and often tack can be reduced significantly. But these emulsions suffer from the disadvantage of often requiring the use of ethanol to achieve desired aesthetics, which has negative environmental regulatory implications. Moreover, these emulsions are relatively expensive. Another disadvantage of these emulsions is the need for precise refractive index matching (for clarity), which gives processing difficulties. In connection with these emulsions, note U.S. Pat. No. 4,673,570 to Soldati and PCT (International Application) Publication No. WO92/05767, the contents of each of which are incorporated herein by reference in their entirety.

U.S. Pat. No. 3,862,310 to Quasius discloses polyethylene mixed polyamines-polyformamides having a molecular weight from 1,800 to 200,000, in which 15–60% of the total nitrogen atoms are present in the formamide groups, these materials having utility in cosmetic compositions, particularly shampoos, rinses and other cosmetic compositions used for cleaning skin or hair and intended to be rinsed away with water. These materials exhibit improved foaming and slower precipitation in use, as well as less scumming of the shampoo and less deposition and build-up of solids on the hair and skin in use. This patent discloses that the cosmetic compositions in which these materials may be employed include shampoos, detergent or soap bars, bubble baths and bath oils, deodorants and antiperspirants, hair dressings, shaving preparation compositions and after-shave lotions, hairsprays and the like.

While disclosing use of specific polyethylene mixed polyamine-polyformamide materials in cosmetic compositions, these materials have an active effect in the cosmetic composition. This patent does not disclose that the materials can act as thickening agents, in forming solid cosmetic compositions.

U.S. Pat. No. 5,270,379 to McAndrew, et al discloses fluid coating materials thickened with hydrophobically-modified amine functional polymers. These polymers are produced by hydrolyzing poly(ethenylformamide) to poly(vinylamine), and then hydrophobically modifying this polymer with an aldehyde such as dodecyl aldehyde. This patent discloses water-based fluid coating materials containing a thickening amount of a polyvinyl amine polymer which has a weight average molecular weight above $10^5$ and which has been modified by reaction with at least 0.2 mer percent of a linear monoaldehyde having 8 to 30 carbon atoms. These functional polymers act as associative thickeners in the fluid coating materials. This patent discloses that the fluid coating materials include within their scope a broad variety of products having the common feature that they must have sufficient body to be applied to a surface and be retained on that surface, while also being sufficiently fluid to form a smooth, coherent film which, in effect, forms a new surface on the old. This patent discloses that the most common coating material of this nature is a water-based latex paint, but this patent discloses that the coating materials include such diverse products as personal care formulations such as emollients and hair conditioning shampoos, pigmented printing inks, paper and textile coatings, and topical medicines.

While disclosing thickening agents for water-based fluid coating materials, the polymers in U.S. Pat. No. 5,270,379 require hydrophobic units which are critical to the gelling abilities of these polymers. Moreover, U.S. Pat. No. 5,270, 379 does not disclose solid cosmetic compositions, much less thickening agents for solid compositions. In addition, this patent does not disclose thickening agents for compositions containing antiperspirant active aluminum-containing materials, which agents are stable in acidic environments occurring with various conventional antiperspirant active aluminum-containing materials.

Accordingly, there is still a need for providing a stable cosmetic composition (e.g., a liquid or gel or stick deodorant and/or antiperspirant composition), which can be clear; which provides good flexibility to the formulator and which can be simply and inexpensively manufactured, and which can be easily and effectively applied to the skin of a person.

SUMMARY OF THE INVENTION

It is an object of the present invention to provide a cosmetic composition (liquid or solid, including sticks and gels) containing an antiperspirant active aluminum-containing material, and a method of using this composition.

It is a further object of the present invention to provide a cosmetic composition containing an antiperspirant active aluminum-containing material, which composition is clear, and a method of using this composition.

It is a further object of the present invention to provide a cosmetic composition that does not require refractive index matching to obtain clarity and transparency, leading to more versatility in formulating, and much simpler manufacturing.

It is a further object of the present invention to provide a cosmetic composition having a deodorant effect, the composition containing an antiperspirant active aluminum-containing material.

It is a still further object of the present invention to provide an antiperspirant composition containing an antiperspirant active aluminum-containing material, which composition is stable even in the presence of acidic antiperspirant active aluminum-containing materials (such as conventional aluminum chlorohydrate or conventional aluminum-zirconium salts), which composition can be clear, and a method of using this composition.

It is a still further object of the present invention to provide an antiperspirant gel that contains antiperspirant active aluminum-containing materials, which gel is clear and transparent, and can easily be applied by extruding the gel through pores or slots in a dispensing container.

It is a still further object of the present invention to provide a cosmetic composition (for example, a liquid for solid, including a gel or stick, deodorant composition and/or antiperspirant composition) that can be easily and simply manufactured, and which is inexpensive to manufacture.

It is a still further object of the present invention to provide a cosmetic composition that does not need ethanol as an ingredient, leading to fewer environmental restrictions and easier manufacturing.

The foregoing objects are achieved by the present invention, using poly(ethenylformamide) and/or derivatives of poly(ethenylformamide) as a thickening agent, in a composition containing antiperspirant active aluminum-containing materials and a solvent for these aluminum-containing materials. The poly (ethenylformamide) and/or derivative thereof, incorporated as a thickening agent in the composition of the present invention, is not hydrophobically modified with an aldehyde such as dodecyl aldehyde, as are the agents used in U.S. Pat. No. 5,270,379 to McAndrew, et al.

Where the composition contains the aluminum-containing material in an antiperspirant effective amount (that is, an amount effective to reduce perspiration of a human, e.g., in axillary regions, as compared to the perspiration where such amount of antiperspirant active material is not applied), the composition is an antiperspirant composition. Otherwise, where, for example, lesser amounts of the aluminum-containing material are incorporated in the composition, the aluminum-containing material can have a deodorant effect (for example, as a bactericide), and the composition would be a deodorant composition. The composition of the present invention can contain a sufficient amount of the thickening agent (e.g., poly(ethenylformamide) itself and/or derivatives thereof) such that the composition is a gel or solid; alternatively, the composition can contain an amount of the poly (ethenylformamide) thickening agent such that the composition is a liquid.

Preferably, the compositions according to the present invention also include non-ionic surface active agents (surfactants). The compositions according to the present invention can also include ammonium acetate, to firm up (harden) the composition (that is, compositions according to the present invention containing ammonium acetate are firmer than corresponding compositions not containing the ammonium acetate). It is thought that the ammonium acetate provides additional firmness to the composition through controlled network formation of the aluminum-containing material (e.g., aluminum chlorohydrate), although we do not want to be limited to this theory.

Various conventional components can optionally be included in the cosmetic compositions according to the present invention. These include (but are not limited to) fragrances, bactericides, fungicides, colorants, skin treating and conditioning materials, etc. of course, these materials should not unduly affect clarity and transparency of the product, if it is desired to provide a transparent and clear product.

Compositions according to the present invention can easily be manufactured, for example, by dissolving the poly(ethenylformamide) or derivative thereof in a solvent, preferably with moderate heating to facilitate dissolving; adding perfume; and then adding a solution of the aluminum-containing material. Both the poly (ethenylformamide) and/or derivative thereof, and the aluminum-containing material, are dissolved in solvents during the manufacturing process; these solvents may be the same or may be different. The system immediately thickens, and desirably is stirred to ensure homogeneity; where a gel is formed, the gel does not melt or loosen on heating.

Various procedures can be used for forming the compositions of the present invention, e.g., to form gels according to the present invention. Invariably, best results are achieved by combining two solution phases (e.g., two clear solution phases), a phase containing the aluminum-containing material (e.g., aluminum salt) and a phase containing the poly (ethenylformamide) and/or derivative thereof, which phases have already been homogenized. Other ingredients, such as surfactants or fragrances, can be added to either phase before mixing the phases, and the order of addition may be varied. Alternatively, fragrance and/or surfactants may be added after the two phases have been mixed. Heating may be applied when forming the compositions of the present invention, although such heating is not always necessary. The foregoing procedure is illustrative of a technique for forming the compositions of the present invention, and is not limiting.

The compositions according to the present invention can be packaged in conventional dispensing packages for the appropriate dosage form, using conventional techniques.

The compositions according to the present invention are used as conventional cosmetic compositions (for example, conventional liquid or solid antiperspirant compositions) are used. For example, where the composition according to the present invention is a gel antiperspirant composition, packaged in a dispensing container having a top surface with slots or pores, the gel is extruded from the dispensing container through the slots or pores and applied to the skin (for example, in axillary regions of the human body) by rubbing the gel material extruded through the top surface of the container on the skin in the axillary regions.

Accordingly, by the present invention a cosmetic composition (for example, an antiperspirant composition, such as an antiperspirant gel) can be provided which can be clear and transparent; and, formulated as a gel, is easy to extrude through slots or pores of a conventional dispensing container. The composition is easy to manufacture, and does not require refractive index matching to obtain transparency, leading to more versatility in formulating and much simpler manufacturing. Also, the compositions according to the present invention are relatively inexpensive, especially as compared to conventional emulsion-type antiperspirant gels, and do not require ethanol as an ingredient, leading to fewer environmental restrictions and easier manufacturing. The compositions according to the present invention are stable in acidic environments conventionally associated with antiperspirant active aluminum-containing materials (e.g., aluminum salts).

DETAILED DESCRIPTION OF THE INVENTION

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present disclosure, the present invention is described primarily in connection with a stick or gel antiperspirant composition, including stick or gel clear antiperspirant compositions. However, the present invention is not limited to stick or gel compositions or to antiperspirant compositions (that is, the present invention is not limited to a composition containing an antiperspirant effective amount of the active antiperspirant aluminum-containing material). For example, the composition according to the present invention can be a liquid composition and/or a deodorant composition. Moreover, depending on additional active ingredients included in the composition, the composition can also be an emollient composition, a sunscreen composition, etc. Various active materials incorporated in cosmetic compositions are disclosed in U.S. Pat. No. 4,322,400 to Yuhas, the contents of which are incorporated herein by reference in their entirety.

Throughout the present specification, "active antiperspirant" and "active deodorant" materials are discussed. Both types of materials contribute to reduction of body (e.g., axillary) malodor. By reduction of body malodor, we mean that, generally, there is less body malodor after application of the composition to the person's skin, as compared to the person's body malodor without application of the composition. Such reduction can be due to a masking of the malodor, absorption and/or chemical reaction of the malodorous material, reduction of levels of the bacteria producing the malodorous materials, e.g., from perspiration, reduction of perspiration, etc. The antiperspirant active materials, when utilized in an antiperspirant effective amount in the composition, act to reduce body malodor by reducing production of perspiration; however, these antiperspirant active materials can also have a deodorant function, e.g., as an antimicrobial agent. The deodorant active materials do not substantially reduce the production of perspiration, but reduce malodor in other ways, e.g, as fragrances masking the malodor or reducing the malodor intensity, as odor absorbents, as antimicrobial agents, as agents chemically reacted with malodorous materials, etc.

Throughout the present specification, where compositions are described as including or comprising specific components or materials, it is contemplated by the inventors that the compositions of the present invention also consist essentially of, or consist of, the recited components or materials. Accordingly, throughout the present disclosure any described composition of the present invention can consist essentially of, or consist of, the recited components or materials.

A desired feature of the present invention is that a clear, or transparent, cosmetic composition (e.g., clear or transparent deodorant or antiperspirant composition) can be provided. The term clear or transparent (that is, clarity), according to the present invention, is intended to connote its usual dictionary definition; thus, a clear, e.g., stick or gel antiperspirant composition of the present invention allows ready viewing of objects behind it. By contrast, a translucent composition, although allowing light to pass through, causes the light to be scattered so that it will be impossible to see clearly objects behind the translucent composition.

Within the context of this invention, a composition (for example, an antiperspirant gel) is deemed to be transparent or clear if the maximum transmittance of light of any wavelength in the range 400 to 800 nm through a sample 1 cm thick is at least 35%, preferably at least 50%. The gel is deemed translucent if the maximum transmittance of such light through the sample is between 2% and less than 35%. The composition is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application Publication No. 291,334 A2.

The present invention contemplates a composition containing an antiperspirant active aluminum-containing material (such as aluminum chlorohydrate or aluminum-zirconium salts) and a solvent for this aluminum-containing material, the composition further including poly(ethenylformamide) and/or derivatives thereof as a thickening agent for the composition. Depending on the amount of thickening agent incorporated in the composition, the composition can be a solid (e.g., a stick), a gel, a liquid, etc. The composition also includes a solvent for the poly(ethenylformamide) and/or derivative thereof. Where the composition is a stick or gel, the composition includes a sufficient amount of the thickening agent (which can be the poly(ethenylformamide) and/or derivatives thereof by itself) such that the composition forms a stick or gel. Where the composition contains an antiperspirant effective amount of the aluminum-containing material, the composition is an antiperspirant composition. Illustratively, the composition of the present invention, containing an antiperspirant effective amount of the antiperspirant active, aluminum-containing material (e.g., antiperspirant active aluminum salt), can be applied to axillary regions of the human body so as to reduce perspiration therefrom.

Illustratively, the poly(ethenylformamide) and/or derivative thereof, which can be used as the thickening agent according to the present invention, has the following structure:

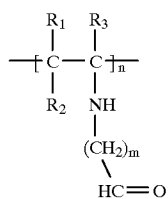

where m is 0–5 inclusive; $R_1$, $R_2$ and $R_3$ are independently H, $C_qH_{2q+1}$, q being 1–5 inclusive, phenyl, $OR_4$ where $R_4$ is $C_qH_{2q+1}$, q being 1–5 inclusive, $(C_2H_4O)_xCH_3$, where x is 1–100 inclusive, $(C_2H_4O)_xH$, where x is 1–100 inclusive, and $C_qH_{2q}OH$, q being 1–5 inclusive; and n has a value such that the polymer has a molecular weight (specifically, weight average ($M_w$), measured using gel permeation chromatography), of 1,000–1,000,000 inclusive. A narrower range for the molecular weight of the polymer, using the same measurement technique, is 50,000–400,000 inclusive. Preferably, the molecular weight is at the lower end of this range (50,000–100,000 inclusive), since polymers in this lower molecular weight range provide solid gels with superior properties (that is, they tend to form less rubbery gels). However, solid cosmetic compositions containing poly(ethenylformamide) at the higher end of the foregoing molecular weight range (that is, having a molecular weight in the range of 300,000–400,000, and above) are also within the present invention.

Mixtures of the poly(ethenylformamide) and derivatives thereof, or mixtures of different derivatives thereof, or mixtures of the polymer and/or derivatives having different molecular weight, can be used as the thickening agent according to the present invention.

The poly(ethenylformamide), also known as poly(N-vinylformamide), has the following general structure:

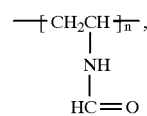

where n, in the foregoing general structure, has a value such that the polymer has a molecular weight (specifically, weight average ($M_w$), measured using gel permeation chromatography) in the range of 1,000–1,000,000 inclusive. The narrower and preferred ranges for the molecular weight, discussed previously, are applicable here.

Poly(ethenylformamide) polymer which can be used as the thickening agent according to the present invention is available from Air Products and Chemicals, Inc. as Experimental Polymer RP-690-11890-1602, and has been assigned CAS #72018-12-3. This polymer has a $T_g$ of about 140–150° C., and decomposes above 225° C. It is fully soluble in all molecular weights in water, formamide and DMSO, is partially soluble in ethylene glycol, and can be hydrolyzed with acid or base to yield pendant primary amine functionality. This polymer has an appearance of a transparent aqueous solution or white powder. The polymer has a pH, in a 4% solution, of 6.5–7.5. Poly(ethenylformamide) at the lower end of the molecular weight range (50,000–100,000) has an intrinsic viscosity (dl/g) of 0.3–0.4 and a Brookfield viscosity (cps, 4% aq. sol'n., 20° C.) of 4–10. Poly(ethenylformamide) at the upper end of the molecular weight range (300,000–400,000) has an intrinsic viscosity (dl/g) of 1.1–1.2 and a Brookfield viscosity (cps, 4% aq. sol'n., 20° C.) of 20–50.

Illustratively, and not limiting, the poly(ethenylformamide) is incorporated in the solid composition in an amount of 0.5–10% by weight, more narrowly 1%–8% by weight, of the total weight of the composition. The viscosity of the composition (e.g., gel) can be controlled by varying the level of the poly(ethenylformamide); higher levels (4%–10%, illustratively) lead to hard, solid gels. Lower levels (e.g., 0.5%–5%) lead to softer gels.

Any of the known antiperspirant active-aluminum-containing materials can be utilized as the antiperspirant active aluminum-containing material of the composition of the present invention. Suitable materials which may be mentioned by way of example include aluminum chlorohydrate, aluminum chloride, aluminum sesquichlorohydrate, aluminum-zirconium hydroxychlorides, complexes or adducts of the above-mentioned active ingredients with glycols, such as propylene glycol (for example, "Rehydrol" II from Reheis Chemical Co.), and combinations thereof. Known aluminum-zirconium salts in combination with neutral amino acids, such as glycine (e.g., aluminum-zirconium tetrachlorohydrex Gly) can also be used. Generally, any of the Category I active antiperspirant ingredients containing aluminum, listed in the Food and Drug Administration's Monograph on Antiperspirant Drug Products for over-the-counter human use (Oct. 10, 1973), can be used. In addition, any new ingredient, not listed in the monograph, such as aluminum nitratohydrate and its combination with zirconyl hydroxychlorides and nitrates or aluminum-stannous chlorohydrates, can be incorporated as an antiperspirant active ingredient in antiperspirant compositions according to the present invention.

Illustratively, and not limiting, the aluminum-containing material is included in the composition in an amount of 3%–40%, more narrowly 15%–25%, by weight, of the total weight of the composition. As can be appreciated, at lower levels the aluminum-containing material (e.g., aluminum salt) acts as a deodorant active material, not an antiperspirant active material, since it is included in the composition in an insufficient amount to reduce flow of perspiration.

Compositions according to the present invention also include a solvent for the antiperspirant active aluminum-containing materials. The poly(ethenylformamide) and/or derivative is also dissolved in a solvent, which may be the same or a different solvent than that for the aluminum-containing material. An illustrative solvent, although not limiting, is water. Illustratively, the water is a substantial part of the composition (a remaining part of the composition), e.g., 70% by weight, of the total weight of the composition.

Solvents other than water, for the aluminum-containing material and/or for the poly(ethenylformamide) and/or derivative thereof, may be used. Poly(ethenylformamide) and derivatives thereof are soluble in a range of solvents including water, propylene glycol, ethylene glycol and water/ethanol 25/75 blends. While the poly (ethenylformamide) and/or derivative thereof may be dissolved in one solvent system (e.g., water) and the aluminum-containing material in another solvent system (e.g., propylene glycol), the two solvent systems must be miscible for gel formation to occur.

Suitable gels according to the present invention can be made using the following solvent systems: water; propylene glycol; blends of water and propylene glycol; and blends of water and ethanol. Where propylene glycol is used, gels formed may be opaque rather than clear.

Preferably, the composition according to the present invention also includes a non-ionic surfactant. The non-ionic surfactant (e.g., polysorbate 20) is added mainly to emulsify the fragrance; however, the addition of non-ionic surfactant also leads to increased gel thickening. The non-ionic surfactants that can be used are those generally known in the art, and include mono-and diglycerides; sorbitol fatty acid esters; polyoxyethylene sorbitan fatty acid esters; polyoxyethylene sorbitol esters; polyoxyethylene acids; polyoxyethylene alcohols; polyoxyethylene adducts; polymeric surfactants; and mixtures thereof. This list is not exhaustive, but rather illustrative, and other non-ionic surfactants can also be utilized. For various non-ionic surfactants, appropriate for cosmetic compositions according to the present invention, see U.S. Pat. No. 4,948,578 to Burger, et al, the contents of which are incorporated herein by reference in their entirety.

Illustrative specific non-ionic surfactants include glyceryl stearate and PEG-100 stearate (Arlacel 165, from ICI Americas); sorbitan laurate (Arlacel 20, from ICI Americas and Span 20 from ICI Americas); polysorbate 20 (Tween 20, from ICI Americas); PEG-40 sorbitan peroleate (Arlatone T, from ICI Americas); PEG-40 stearate (Myrj 52, from ICI Americas); laureth-4 (Brij 30, from ICI Americas); PEG-25 hydrogenated castor oil (Arlatone G, from ICI Americas); and C11-15 Pareth-20 (Tergitol 15-S-20, from Union Carbide).

These non-ionic surfactants can be incorporated in the composition in amounts of 0–20% by weight, of the total weight of the composition. As can be appreciated, these non-ionic surfactants are optional ingredients.

In order to further firm up the solid composition, the composition can also include ammonium acetate, for example, in amounts of 2%–15% by weight, of the total weight of the composition. By addition of sufficient ammonium acetate, a solid antiperspirant stick can be provided.

Illustratively, at compositions containing, for example, in percent by weight of the total weight of the composition, 1% poly(ethenylformamide), 35% water, 46% of a 50% aqueous solution of aluminum chlorohydrate, and 15% of a 4M ammonium acetate solution, a firm gel that is clear is provided. Lesser amounts of ammonium acetate provide a softer gel.

Where the pH of the compositions was reduced, e.g., by adding small amounts of HCl, gels of lower viscosity resulted. As can be seen, various techniques can be used to modify the viscosity of the solid compositions of the present invention.

As indicated previously, minor amounts of various optional ingredients can be included in the composition, including fragrance (for example, in an amount of 0–3% by weight, of the total weight of the composition), colorants, bactericides, fungicides, etc. Various optional ingredients are disclosed in each of U.S. Pat. No. 5,258,174 to Schebece, the contents of which are incorporated herein by reference in their entirety, and the aforementioned U.S. Pat. No. 4,948,578 to Burger, et al, whose contents have already been incorporated herein by reference in their entirety.

The solid compositions according to the present invention illustratively are in the form of a gel. It is difficult to quantitatively distinguish between a cosmetic "gel" and a cosmetic "stick". For example, note the discussion in the article by Schmolka, "Gel Cosmetics" in *Cosmetics & Toiletries,* Vol. 99 (November 1984), pages 69–76. Generally, a gel is more viscous than a liquid, or than a paste which fails to retain its shape. It is not as rigid as a stick. Typically, it is understood that gels are soft, deformable products while sticks are free-standing solids.

Almdale, et al (*Polymer Gels and Networks,* Vol. 1, No. 5, (1993)) list two criteria for defining a system as a gel: (1) a gel consists of two or more components, one of which is a liquid, present in substantial quantities; and (2) a gel is a soft, solid or solid-like material. This latter requirement can be described more accurately through rheological measurement. Typically, gels possess a storage modulus $G'(w)$ which exhibits a pronounced plateau at higher frequencies (on the order of seconds) and a loss modulus $G''(w)$ which is considerably smaller than the storage modulus in one plateau region. In the strict sense, the term "gel" applies to systems having a value $G'(w)$ that is higher than its value of $G''(w)$ at low frequencies; in practice, however, many products marketed as "gels" are truly viscous liquids (for example, some toothpastes).

In the cosmetics field, systems are classified as gels or sticks depending on their viscosity or hardness alone; typically, it is understood that gels are soft, deformable products while sticks are strictly free-standing solids. For example, by rheological analysis, a commercial deodorant stick has been determined to have a plateau storage modulus $G'(w)$ of roughly $10^5$ Pa and a complex viscosity of $10^6$ Pa second (both at an angular frequency of 0.1 rad/sec). On the other hand, a commercial antiperspirant gel has been determined to have a $G'(w)$ value of roughly $10^3$ Pa and a complex viscosity of $10^4$ Pa second (at 0.1 rad/sec).

Rheological parameters such as the storage modulus $G'(w)$ can be measured as a function of angular frequency with a parallel-plate rheometer. For example, such parameters can be generated using a Carrimed CLS 100 Rheometer, using a 2 cm stainless steel plate and a 1 mm sample gap; and over a range of 0.2 to 100 rad/sec at 25° C., using a 1% strain. The principals of rheology and their applications to cosmetic products are reviewed in *Rheological Properties of Cosmetics and Toiletries,* Dennis Laba, Ed. (1993).

Illustratively, where the solid composition according to the present invention is a gel, the gel has a viscosity from about 100 to 500,000 cps (measurements being made using a Brookfield RV viscometer with spindle F at 2.5 RPM), or about 2,000 to about 300,000 cps (measurements being made using a Brookfield RVT viscometer with Spindle D at 2.5 RPM). It is emphasized that these ranges are illustrative, and are not essential in connection with the present invention.

The composition according to the present invention can be made by the following procedure, this procedure being illustrative and not limiting of the present invention. The poly(ethenylformamide) is dissolved in water (this is facilitated with moderate heating). Thereafter, a non-ionic surfactant (for example, Tween 20) and perfume are added while the system cools. Finally, an aqueous solution of the antiperspirant active aluminum-containing material (for example, aluminum chlorohydrate) is stirred into the system at room temperature. The system immediately thickens, and is stirred to ensure homogeneity. The gel does not "melt" or loosen on heating.

While the gel does increase dramatically in viscosity initially, it appears that the viscosity stabilizes after 24 hours. Gels of identical compositions, aged one day and one month at room temperature, both exhibited viscosities of roughly 220,000 cps (measured by a Brookfield RV Viscometer with spindle F at 2.5 RPM).

The cosmetic composition according to the present invention can be packaged in conventional packages, using conventional techniques. For example, where a gel cosmetic composition is produced, the gel can be introduced into a dispensing package (for example, a package having a top surface with slots or pores), as conventionally done in the art.

Thereafter, the product can be dispensed from this dispensing package, by extruding product from the dispensing package onto the top surface, through the pores or slots, and then rubbing the exposed gel on the skin (for example, on skin in the axillary regions), so as to deposit the active material (for example, antiperspirant active aluminum-containing material) on the skin. This provides good deposition of the antiperspirant active aluminum-containing material, as well as other active materials, on the skin.

In the following, specific examples of compositions within the scope of the present invention are set forth. Of course, these specific examples are illustrative of the present invention, and are not limiting. In the following examples, as well as throughout the present specification, names utilized are the CTFA (Cosmetics, Toiletry and Fragrance Association, Inc.) names, as set forth in the *CTFA International Cosmetic Ingredient Dictionary* (4th Ed. 1991), the contents of which dictionary are incorporated herein by reference in their entirety.

In the examples, the compositions were formed by forming a solution of the poly(ethenylformamide) in the solvent therefor (water, propylene glycol or water/propylene glycol); and, thereafter, slowly adding this solution of poly(ethenylformamide) to a solution of the antiperspirant active material. Where fragrance and non-ionic surfactant were incorporated in the composition in these examples, the fragrance and non-ionic surfactant were incorporated with the solution of the antiperspirant active material, and, thereafter, the solution of poly(ethenylformamide) was mixed into the solution of the antiperspirant active material.

EXAMPLE I

| Component | %, by weight |
|---|---|
| Aluminum chlorohydrate (50% aq sol'n) (Chlorhydrol) | 20.00 |
| Water | 76.00 |
| Poly(ethenylformamide) | 4.00 |
| ($M_w$ = 72,000) | |
| | 100.00 |

The composition formed was a clear, soft gel.

EXAMPLE II

| Component | %, by weight |
|---|---|
| Al—Zr Tetrachlorohydrex GLY (36% aq sol'n) (Rezal 36) | 55.00 |
| Water | 41.00 |
| Poly (ethenylformamide) | 4.00 |
| ($M_w$ = 72,000) | |
| | 100.00 |

The composition formed was a stiff, brittle gel.

EXAMPLE III

| Component | %, by weight |
|---|---|
| Al=Zr Tetrachlorohydrex GLY (36% aq sol'n) (Rezal 36) | 55.00 |
| Water | 43.00 |
| Poly(ethenylformamide) | 2.00 |
| ($M_w$ = 72,000) | |
| | 100.00 |

The composition formed was a clear, soft gel, which was very viscous.

EXAMPLE IV

| Component | %, by weight |
|---|---|
| Al—Zr Tetrachlorohydrex GLY (36% aq sol'n) (Rezal 36) | 27.50 |
| Water | 66.50 |
| Poly(ethenylformamide) | 6.00 |
| ($M_w$ = 72,000) | |
| | 100.00 |

The composition formed was a hard, rubbery gel.

EXAMPLE V

| Component | %, by weight |
| --- | --- |
| Al—Zr Tetrachlorohydrex GLY (36% aq sol'n) (Rezal 36) | 27.50 |
| Water | 68.50 |
| Poly(ethenylformamide) ($M_w$ = 72,000) | 4.00 |
| | 100.00 |

The composition formed was soft and somewhat rubbery.

EXAMPLE VI

| Component | %, by weight |
| --- | --- |
| Al—Zr Tetrachlorohydrex GLY (36% aq sol'n) (Rezal 36) | 55.00 |
| Water | 42.50 |
| Poly(ethenylformamide) ($M_w$ = 72,000) | 2.50 |
| | 100.00 |

The product formed was a soft, clear gel.

EXAMPLE VII

| Component | %, by weight |
| --- | --- |
| Aluminum chlorohydrate (50% aq sol'n) (Chlorhydrol) | 50.00 |
| Water | 41.20 |
| Poly(ethenylformamide) ($M_w$ = 72,000) | 2.00 |
| Polysorbate 20 (Tween 20) | 6.00 |
| Fragrance | 0.80 |
| | 100.00 |

The product formed was a soft, extrudable clear gel.

EXAMPLE VIII

| Component | %, by weight |
| --- | --- |
| Aluminum chlorohydrate (50% aq sol'n) | 46 |
| Water | 38 |
| Poly(ethenylformamide) ($M_w$ = 50,000) | 1 |
| 4M ammonium acetate | 15 |
| | 100 |

The composition of Example VIII was produced by first dissolving the poly(ethenylformamide) into the water, followed by the addition of the aqueous aluminum chlorohydrate solution and finally the ammonium acetate. The solutions were rolled to mix the ammonium acetate evenly, since the systems were very viscous for stirring with a stir bar.

The product formed was a clear, firm gel, slightly slippery and slightly tacky.

Desirably, where ammonium acetate is included in the composition, the composition includes relatively small amounts (e.g., 1% by weight, of the total weight of the composition) of the poly(ethenylformamide), so as to avoid a composition so viscous, after mixing the polymer and aluminum-containing material solutions, that addition of the ammonium acetate is difficult. As the amount of ammonium acetate incorporated in the composition increases, the firmness of the final gel increases.

EXAMPLE IX

| Component | %, by weight |
| --- | --- |
| Aluminum chlorohydrate | 20 |
| Water | 71 |
| Poly(ethenylformamide) ($M_w$ = 72,000) | 2 |
| Polysorbate 20 (Tween 20) | 6 |
| Perfume | 1 |
| | 100 |

The product formed was a soft, extrudable clear gel.

EXAMPLE X

| Component | %, by weight |
| --- | --- |
| Aluminum chlorohydrex PG (30% PG) (Rehydrol II) | 50.00 |
| Propylene glycol | 46.00 |
| Poly(ethenylformamide) ($M_w$ = 72,000) | 4.00 |
| | 100.00 |

A solution of the poly(ethenylformamide) in the propylene glycol was provided by heating to 40°–50° C. to speed up solubilization, together with mixing. The solution of the poly(ethenylformamide) in propylene glycol was then added to the Rehydrol II. A soft opaque homogeneous gel resulted.

EXAMPLE XI

| Component | %, by weight |
| --- | --- |
| Aluminum chlorohydrex PG (30% PG) (Rehydrol II) | 20.00 |
| Water | 38.50 |
| Propylene glycol | 38.50 |
| Poly(ethenylformamide) ($M_w$ = 72,000) | 3.00 |
| | 100.00 |

Initially, a slightly turbid gel, with some separation evident, resulted. Thereafter, the gel became clear and homogeneous.

EXAMPLE XII

| Component | %, by weight |
| --- | --- |
| Aluminum chlorohydrate (50% aq sol'n) (Chlorhydrol) | 40.00 |
| Water | 47.00 |

-continued

| Component | %, by weight |
| --- | --- |
| ethanol | 10.00 |
| Poly(ethenylformamide) | 3.00 |
| ($M_w$ = 72,000) | |
| | 100.00 |

Initially, a soft turbid gel resulted, which was not homogeneous. Thereafter, the gel became clear and homogeneous.

EXAMPLE XIII

| Component | %, by weight |
| --- | --- |
| Aluminum chlorohydrex PG (30% PG) (Rehydrol II) | 15.00 |
| Water | 41.00 |
| Propylene glycol | 41.00 |
| Poly(ethenylformamide) | 3.00 |
| ($M_w$ = 72,000) | |
| | 100.00 |

The resulting composition was a clear and viscous liquid.

EXAMPLE XIV

| Component | %, by weight |
| --- | --- |
| Aluminum chlorohydrate (50% aq sol'n) (Chlorhydrol) | 50.00 |
| Water | 49.00 |
| Poly(ethenylforinamide) | 1.00 |
| ($M_w$ = 409,000) | |
| | 100.00 |

The resulting composition was a homogeneous, soft clear gel.

EXAMPLE XV

| Component | %, by weight |
| --- | --- |
| Aluminum chlorohydrate (50% aq sol'n) (Chlorhydrol) | 10.0 |
| Water | 84.0 |
| Poly(ethenylformamide) | 6.0 |
| ($M_w$ approx. 400,000) | |
| | 100.00 |

The composition was a hard, rubbery clear gel. This is an example of a composition containing a lower content of aluminum salt (e.g., a deodorant gel), and an example of a composition containing a high molecular weight poly (ethenylformamide).

Thus, according to the present invention, a cosmetic composition, which can be provided as a solid or liquid clear composition (e.g., stick or gel), containing antiperspirant active aluminum-containing materials, can be achieved. This composition can be provided as, for example, a clear and transparent gel, easy to extrude through pores or slots of the dispensing container. The compositions according to the present invention are stable, even in the presence of a conventional antiperspirant active aluminum-containing salt such as aluminum chlorohydrate or aluminum-zirconium tetrachlorohydrex-gly. In addition, compositions according to the present invention can be easily and simply manufactured, and are relatively inexpensive. Moreover, since compositions according to the present invention achieve clarity by means other than refractive index matching as in conventional antiperspirant emulsion gels, there is much more versatility in formulating the compositions. Furthermore, there is no need for incorporating ethanol as an ingredient in the composition (although ethanol may be incorporated as an ingredient), leading to reduced environmental restrictions and easier manufacturing.

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

We claim:

1. A cosmetic composition, comprising an antiperspirant active aluminum-containing material, a solvent for the antiperspirant active aluminum-containing material, and a component selected from the group consisting of poly (ethenylformamide) and derivative thereof as a thickening agent for the composition, the thickening agent being included in the composition in an amount sufficient to thicken the composition.

2. A cosmetic composition according to claim 1, further comprising a solvent for said component.

3. A cosmetic composition according to claim 1, wherein the thickening agent is included in the composition in a sufficient amount such that the composition is a stick or gel composition.

4. A cosmetic composition according to claim 1, wherein the antiperspirant active aluminum-containing material is an antiperspirant active aluminum-containing salt.

5. A cosmetic composition according to claim 4, wherein the antiperspirant active aluminum-containing salt is incorporated in the composition in an amount so as to have a deodorant effect when applied to a human body, whereby a solid deodorant composition is provided.

6. A cosmetic composition according to claim 1, wherein the solvent for the antiperspirant active aluminum-containing material is also a solvent for said component.

7. A cosmetic composition according to claim 1, wherein the composition is clear.

8. A cosmetic composition according to claim 1, wherein the composition further includes ammonium acetate in an amount to harden the cosmetic composition.

9. A cosmetic composition according to claim 1, further comprising a non-ionic surfactant.

10. A cosmetic composition according to claim 1, wherein said component has a formula

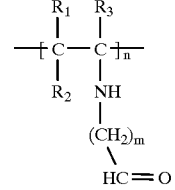

where m is 0–5; $R_1$, $R_2$ and $R_3$ are independently H, $C_qH_{2q+1}$, q being 1–5 inclusive, phenyl, $OR_4$, where $R_4$ is $C_{2q+1}$, q being 1–5 inclusive, $(C_2H_4O)_xCH_3$, where x is 1–100, $(C_2H_4O)_xH$, where x is 1–100, and $C_qH_{2q}OH$, q being 1–5 inclusive, and n has a value such that the component has a weight average molecular weight, measured using gel permeation chromatography, of 1,000–1,000,000.

11. A cosmetic composition according to claim 10, wherein the formula is

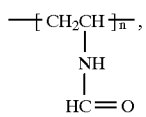

n being previously defined.

12. An antiperspirant composition, comprising an antiperspirant active aluminum-containing material, a solvent for the aluminum-containing material, and a component selected from the group consisting of poly(ethenylformamide) and derivatives thereof as a thickening agent, the antiperspirant active aluminum-containing material being included in the composition in an antiperspirant effective amount, and the thickening agent being included in the composition in an amount sufficient to thicken the composition.

13. An antiperspirant composition according to claim 12, further comprising a solvent for said component.

14. An antiperspirant composition according to claim 12, wherein the thickening agent is included in the composition in a sufficient amount such that the composition is a stick or gel composition.

15. An antiperspirant composition according to claim 12, wherein said antiperspirant active aluminum-containing material is an antiperspirant active aluminum-containing salt.

16. An antiperspirant composition according to claim 15, wherein the aluminum-containing salt is selected from the group consisting of antiperspirant active aluminum salts and antiperspirant active aluminum-zirconium salts.

17. An antiperspirant composition according to claim 15, wherein said solvent is water.

18. An antiperspirant composition according to claim 17, wherein the composition further includes a non-ionic surfactant.

19. An antiperspirant composition according to claim 18, wherein the non-ionic surfactant is selected from the group consisting of monoglycerides, diglycerides, sorbitan fatty acid esters, polyoxyethylene sorbitan fatty acid esters, polyoxyethylene sorbitol esters, polyoxyethylene acids, polyoxyethylene alcohols, polyoxyethylene adducts, polymeric surfactants and mixtures thereof.

20. An antiperspirant composition according to claim 17, wherein the composition include 0.5–10% by weight, of the total weight of the composition, of said component.

21. An antiperspirant composition according to claim 20, the composition including, in percent by weight of the total weight of the composition, 3%–40% by weight antiperspirant active aluminum-containing salt, 0%–20% non-ionic surfactant, 0%–3% fragrance, and balance water.

22. An antiperspirant composition according to claim 12, said composition being clear.

23. An antiperspirant composition according to claim 22, wherein said composition is a gel.

24. An antiperspirant composition according to claim 23, wherein said gel has a viscosity from about 100–500,000 cps, as measured using a Brookfield RV viscometer with spindle F at 2.5 RPM.

25. An antiperspirant composition according to claim 12, wherein said component has a molecular weight, as measured using gel permeation chromatography, from about 1,000–1,000,000.

26. An antiperspirant composition according to claim 25, wherein the molecular weight of said component is from about 50,000–100,000.

27. An antiperspirant composition according to claim 25, wherein the molecular weight of said component is from about 300,000–400,000.

28. An antiperspirant composition according to claim 12, wherein the composition further comprises ammonium acetate, in an amount so as to harden the composition.

29. An antiperspirant composition according to claim 28, wherein the composition includes ammonium acetate in an amount of 2%–15% by weight, of the total weight of the composition.

30. An antiperspirant composition according to claim 29, wherein the solvent is water.

31. An antiperspirant composition according to claim 30, wherein the composition is a clear composition.

32. An antiperspirant composition according to claim 12, wherein said component has a formula

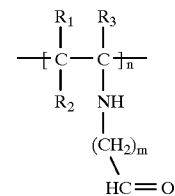

where m is 0–5; $R_1$, $R_2$ and $R_3$ are independently H, $C_qH_{2q+1}$, q being 1–5, phenyl, $OR_4$, where $R_4$ is $C_{2q+1}$, q being 1–5, $(C_2H_4O)_xCH_3$, where x is 1–100, $(C_2H_4O)_xH$, where x is 1–100, and $C_8H_{2q}OH$, q being 1–5, and n has a value such that the material has a weight average molecular weight, measured using gel permeation chromatography, of 1,000–1,000,000.

33. An antiperspirant composition according to claim 32, wherein the formula is

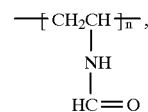

n being previously defined.

34. A cosmetic composition, comprising, in percent by weight of the total weight of the composition:
(a) 0.5%–10% of a component selected from the group consisting of poly(ethenylformamide) and derivatives thereof;
(b) 3%–40% antiperspirant active aluminum-containing salt;
(c) 0%–20% non-ionic surfactant;
(d) 0%–3% fragrance; and
(e) balance water.

35. A cosmetic composition according to claim 34, wherein the antiperspirant active aluminum-containing salt is selected from the group consisting of antiperspirant active aluminum salts and antiperspirant active aluminum-zirconium salts.

36. A cosmetic composition according to claim 35, wherein the non-ionic surfactant is selected from the group consisting of polysorbate 20 and C11-15 Pareth-15.

37. A cosmetic composition according to claim 34, wherein said component has a formula

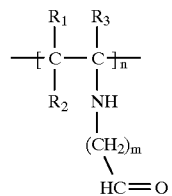

where m is 0–5; $R_1$, $R_2$ and $R_3$ are independently H, $C_qH_{2q+1}$, q being 1–5, phenyl, $OR_4$, where $R_4$ is $C_{2q+1}$, q being 1–5, $(C_2H_4O)_xCH_3$, where x is 1–100, $(C_2H_4O)_xH$, where x is 1–100, and $C_8H_{2q}OH$, q being 1–5, and n has a value such that the material has a weight average molecular weight, measured using gel permeation chromatography, of 1,000–1,000,000.

38. A cosmetic composition according to claim 37, wherein the formula is

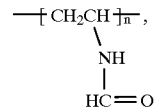

n being previously defined.

39. A method of reducing perspiration from the skin of a human, comprising the step of applying the antiperspirant composition of claim 12 to the skin.

40. The method according to claim 39, wherein the antiperspirant composition is applied to the skin in axillary regions of the human, so as to reduce perspiration in the axillary regions.

* * * * *